United States Patent [19]

Hannah

[11] Patent Number: 4,998,915

[45] Date of Patent: Mar. 12, 1991

[54] ASPIRATING DEVICE

[75] Inventor: Ralph E. Hannah, Sandy, Utah

[73] Assignee: Unimed, Inc., Salt Lake City, Utah

[21] Appl. No.: 473,328

[22] Filed: Feb. 1, 1990

[51] Int. Cl.[5] .............................................. A61M 1/00
[52] U.S. Cl. ..................................... 604/73; 604/181; 604/319
[58] Field of Search .................... 604/73, 93, 118, 119, 604/151, 152, 181, 317, 319, 902

[56] References Cited

U.S. PATENT DOCUMENTS

| | | |
|---|---|---|
| 973,456 | 10/1910 | Neveu . |
| 1,115,107 | 10/1914 | Rice . |
| 2,822,808 | 2/1958 | Boone . |
| 3,018,779 | 1/1962 | Tyler et al. . |
| 3,039,463 | 6/1962 | Dickey, Jr. et al. . |
| 3,319,628 | 5/1967 | Halligan . |
| 3,542,031 | 11/1970 | Taylor . |
| 3,646,935 | 3/1972 | Holbrook et al. . |
| 3,937,220 | 2/1976 | Coyne . |
| 3,957,051 | 5/1976 | Topham . |
| 4,059,111 | 11/1977 | Erasmus ............................. 604/54 |
| 4,275,724 | 1/1981 | Behrstock . |
| 4,317,525 | 2/1982 | Schuessler . |
| 4,334,538 | 6/1982 | Juhn . |
| 4,359,050 | 11/1982 | Reynolds . |
| 4,382,789 | 5/1983 | Colombo . |
| 4,445,517 | 1/1984 | Feild . |
| 4,460,354 | 5/1984 | Weilbacher . |
| 4,539,985 | 9/1985 | Magrath . |
| 4,643,719 | 2/1987 | Garth . |
| 4,684,362 | 8/1987 | Holt . |
| 4,699,138 | 10/1987 | Behrstock . |
| 4,729,764 | 3/1988 | Gualtier . |
| 4,729,765 | 3/1988 | Eckels et al. . |
| 4,915,691 | 4/1990 | Jones et al. .......................... 604/902 |
| 4,921,488 | 5/1990 | Maitz et al. .......................... 604/319 |

Primary Examiner—Stephen C. Pellegrino
Attorney, Agent, or Firm—Sigalos, Levine & Montgomery

[57] ABSTRACT

A hand-held aspirating device comprising a main housing having a handle and a barrel, said barrel having a front end and a rear portion, said handle having a lower end and an upper end communicating with said rear portion of said barrel; actuating means extending from said main housing beneath said barrel, means operatively associated with said actuating means to normally maintain said actuating means in an extended position, said actuating means being actuable in a direction generally parallel to said barrel to move said actuating means rearwardly toward said handle; suction means including a suction chamber disposed within said housing and responsive to the actuation of said actuating means for creating a suction within said suction chamber; a container means for receiving aspirate, said container means being removably connected to said handle; a first conduit within said housing, said first conduit having two ends, one of said ends normally being in fluid-flow communication with said container means and the other end being connected to said suction chamber; a second conduit depending from said front end of said barrel and projecting outwardly therefrom, said second conduit having two ends, one for inserting into a body cavity, the other one end being in fluid-flow communication with said container means; whereby when said actuating means is actuated and said suction is created within said suction chamber, said suction is communicated through said first conduit from said suction chamber to said container means and then through said second conduit to said one of said two ends of said second conduit thereby to aspirate fluids from said body cavity through said second conduit into said container means.

6 Claims, 2 Drawing Sheets

ASPIRATING DEVICE

BACKGROUND OF THE INVENTION

This invention relates to aspirating (e.g., gastric suction) devices and more particularly to those which are both disposable and particularly adapted for collecting fluids from body cavities such as the stomachs of new born infants.

Aspirating devices have heretofore been proposed, illustrative of which are those represented by Holbrook et al U.S. Pat. No. 3,646,935, Dickey et al U.S. Pat. No. 3,039,463, Taylor U.S. Pat. No. 3,542,031, Coyne U.S. Pat. No. 3,937,220 and Halligan U.S. Pat. No. 3,319,628. These patents disclose, inter alia, vacuum operated systems for aspirating fluids from body cavities. According to these proposals, the required suction is either supplied by connection to a separate vacuum production mechanism, often through a connection to a pipe or tube leading to a central system, or through a system that is either cumbersome or which is subject to contamination. Moreover, the proposals of the prior art have embodied structures and configurations which are either not suitable for single use and disposal or which required a separate suction source.

The advent of pernicious infective vectors such as the AIDS virus has heightened the danger of multiple utilization of medical equipment, thus increasing the importance of single use and disposability. Moreover, there is a need for an aspirator that is self contained and independent of any external suction source. Accordingly, there has continued to be a need for an aspirating mechanism which small, light in weight, easily transportable, effective to aspirate fluids from body cavities, inexpensive, independent of external vacuum sources, readily operable by a medical professional single-handedly, sterile, structured so as to avoid any accidental contamination of the user, and so low in cost as to render it attractively disposable.

BRIEF DESCRIPTION OF THE INVENTION

The aspirating device in accordance with the principles of this invention provide in one simple disposable instrument all the foregoing features. Thus, the device is readily operable with one hand by a medical professional, is very low cost, thus making it attractive for disposability, is sterile, independent of external suction sources, reliable and provides a removable sample container into which the aspirated fluids are discharged and retained, thus preventing contamination of the user and making the device attractive not only for the aspiration of the desired fluids, but also providing a ready means of retaining and transporting such fluids for subsequent analysis.

This is accomplished through a unique combination of interrelated elements including a trigger operated suction producing chamber, a sanitary suction tube, and a removable fluid container, all housed within a pistol-shaped housing which provides the required interrelated positioning and support for the component parts so as to facilitate their cooperative interaction during operation.

OBJECTS AND FEATURES

It is one general object of the invention to improve aspirators.

It is another object of the invention to make aspirators both disposable and low cost.

It is another object of the invention to improve and simplify the suction creation and communication segments of a self-contained hand held aspirator.

It is still a further object of the invention to create in a low cost disposable aspirator a mechanism adapted for the cooperative interaction of a removable cup in which aspirate is collected.

Accordingly, in accordance with one feature of the invention, a hand held pistol-shaped aspirator is provided having a trigger in communication with a suction producing chamber and in which the suction of the suction producing chamber is communicated to the exterior through sealed conduits to communicate suction from the suction chamber through an aspirate collection cup, thereby facilitating aspiration, simplifying construction and reducing costs.

In accordance with another feature of the invention, through the channeling of suction through the cup, the aspirate is communicated directly from the exterior to the cup instead of being passed through or in contact with the suction producing mechanism, thus preventing contamination of the aspirate.

In accordance with yet another feature of the invention, an improved suction producing mechanism is provided, thus enhancing operating characteristics and further simplifying construction and reducing costs.

These and other objects and features of the invention will be apparent from the following detailed description, by way of example of a preferred embodiment, with reference to the drawing.

THE DRAWING

DETAILED DESCRIPTION

Figure 1:
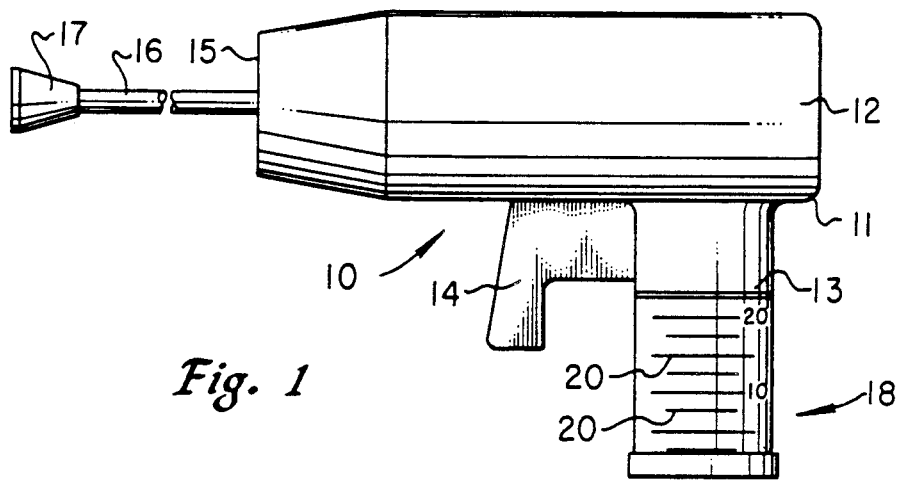
FIG. 1 is a side elevation view of the aspirator constructed in accordance with the principles hereof.

Now turning to the drawing, and more particularly to FIG. 1 thereof, it will be observed that there is therein depicted in the form of a a gastric suction device 10, an aspirator, having a main housing 11, generally in the shape of a pistol, comprising a barrel-shaped member 12 and a handle portion 13 extending downwardly therefrom. Fitted within barrel-shaped member 12 and handle portion 13 and extending outwardly therefrom beneath the barrel is an actuating means 14, suitably a trigger. Also, depending from barrel-shaped member 12 and extending outwardly from the front end 15 thereof is conduit 16 having at its outer extremity an optional adapter 17 provided to optimize contact with a fluid-containing body cavity (not shown). This general pistol-shape permits easy one-hand use of the device by the health care provider; i.e., doctor, nurse, or the like.

At the lower end 18 of handle portion 13 there is disposed container means 19, suitably a cup, removably mounted in handle 13 for receiving aspirate which may or may not be inscribed with gradations 20 that may be useful identifying to the user the quantity of aspirate contents collected within the cup.

Figure 2:
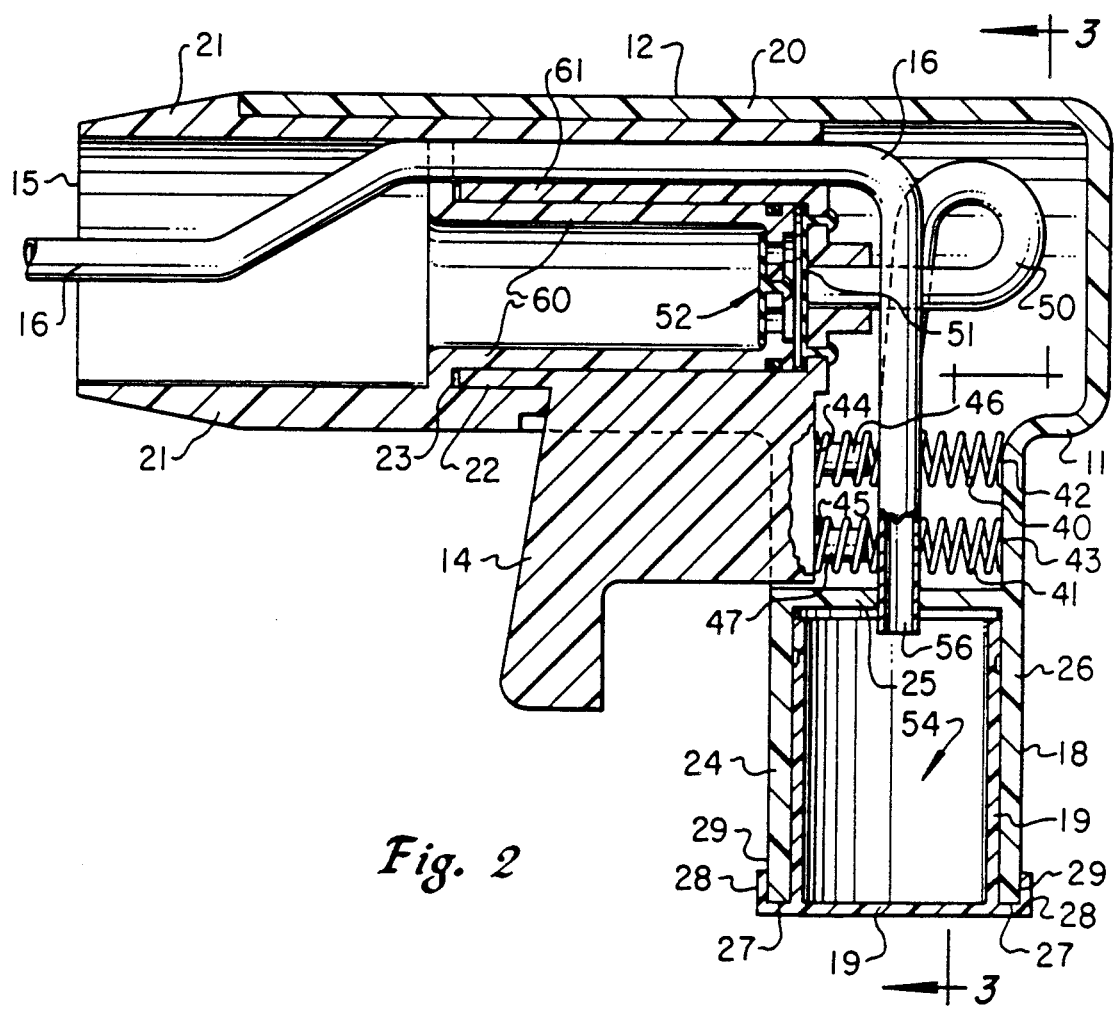
FIG. 2 is a section through the mechanism of FIG. 1, illustrating in detail the internal mechanism and showing that mechanism in the quiescent or unactuated condition.

Now turning to FIG. 2, the mechanism according to the invention is depicted in greater detail. There, it will be seen that the exterior shell comprises two portions 20 and 21 which may be pressed together or sealed together in any of a variety of conventional ways, such as by gluing or cementing. When joined together, portions 20 and 21 present a smooth almost discontinuous appearance from the exterior.

Trigger 14 is seen to include horizontally projecting portion 22, that is slideably disposed within mating recess 23. Since in FIG. 2, horizontally projecting portion 22 is extended almost fully within mating recess 23, mating recess 23 is better shown in FIG. 4, which depicts the trigger as being retracted toward the rear.

The lower end 18 of aspirator main housing 11 includes a cylindrically shaped upwardly extending recess formed by walls 24, 25 and 26. Press fit upwardly within the recess is specimen cup 19 which is fitted with a circumferentially disposed recess 27 formed by upwardly projecting circumferential lip 28. Removable cup 19 is held in place by friction imparted by circumferential lip 18 against the exterior surface of walls 24 and 26.

Removable cup 19 may have an open upper end (as shown) or a partially covered upper end so long as the upper portion provides a passageway for communication of aspirate therethrough. The upper end may be completely covered with an elastomeric membrane (not shown) having a deformable cross-shaped slit therein to allow passage therethrough of conduit 16 to permit conduit 16 to protrude into the interior of removable cup 19. When aspiration is completed cup 19 is removed from the lower end 18 of main housing 11, and the slit will close and seal and not permit the contents of cup 19 to escape. However, it is contemplated that in most instances a completely open ended cup will be employed so as to facilitate the subsequent enclosure thereof by conventional snap fitting cap (not shown).

Lower end 18 of aspirator main housing 11 and cup 19 are preferably made of transparent plastic to enable the user to observe how much fluid is being aspirated into cup 19 and to ensure it does not overflow.

Figure 4:
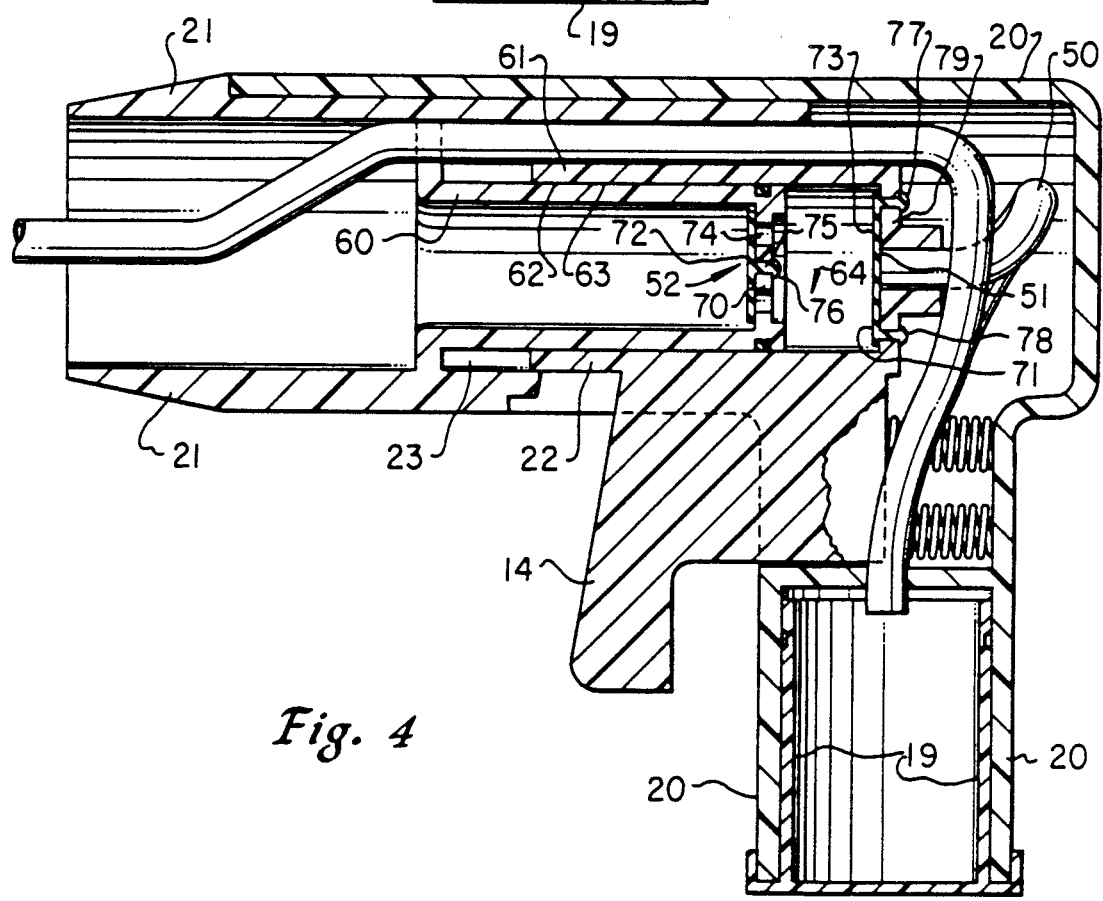
FIG. 4 is a sectional view similar to that of FIG. 2 except showing the aspirator in the actuated condition with the trigger moved toward the rear and with the suction producing chamber extended to produce required suction.

Further reference to FIG. 2 reveals means 40 and 41, preferably a pair of springs, which are disposed horizontally within main housing 11 and which at their rear ends 42 and 43 engage the inner surfaces of main housing 11 and are retained in position at their rear extremities by projecting pins or other conventional means. At their front ends, springs 40 and 41 partially surround and are retained in engagement with rear surfaces 44 and 45 of trigger 44 by projecting pins 46 and 47. As will be observed, pins 46 and 47 are significantly smaller in exterior diameter than the interior diameters of springs 40 and 41, thereby providing for a slideable movement therewithin as trigger 14 is moved toward the rear position as shown in FIG. 4.

Figure 3:
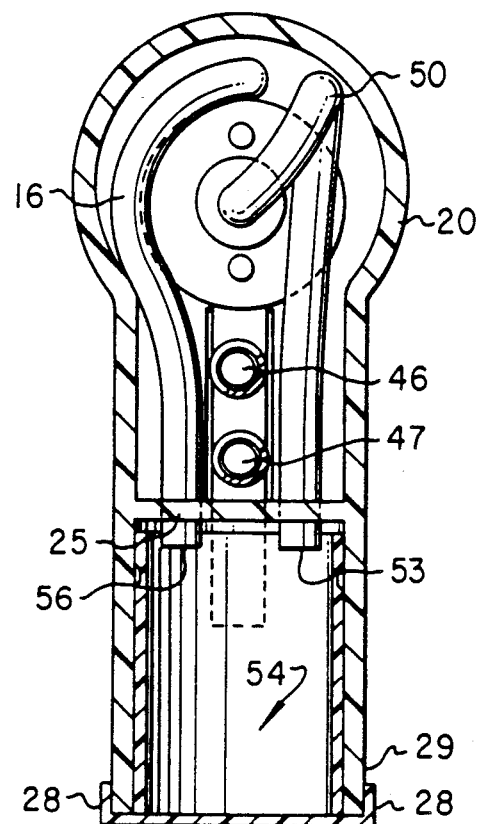
FIG. 3 is a section taken along section lines 3—3 of FIG. 2 further depicting internal details of the aspirator mechanism.

As will be observed from further reference to the figures, there are two principle conduits within the aspirator 10. The first of these is conduit 50 one end 51 of which in communication with a suction production mechanism generally shown at 52, and the other end 53 of which (FIG. 3) is in communication with the interior 54 of removable cup 19, thereby acting to conduct suction produced by suction mechanism 52 to the interior 54 of removable cup 19.

The remaining conduit 16 is seen to project from its extremity 17 inwardly within main housing 11 and thence at its interior extremity projecting downwardly through wall 25 to communicate with the interior 54 of removable cup 19. Thus, when suction is produced within the interior 54 of removable cup 19, such suction is communicated through the interior 56 of conduit 16 and thence to its exterior extremity at adapter 17 so as to impart suction to any object in contact therewith. Accordingly, as mentioned above, such suction is effective when the end of conduit 16 is in communication with a body cavity or the like to suck fluids therefrom and thence through interior 56 of conduit 16 to the interior 54 of removable cup 19.

Further reference to the figures will reveal that the aspirater includes an improved suction producing mechanism which is mentioned above is generally shown at 52. This suction mechanism is comprised of cylindrical intersupport 60 which forms a part of shell portion 21. In sealed sliding relation with interportion 60 is mating exterior cylindrical portion 61 (FIGS. 2 and 4). As will observed from FIG. 2, the suction producing mechanism 52 is in its quiescent or inactive state in which the springs 40 and 41 are effective to project exterior cylindrical portion 61 in its forward most position as shown in FIG. 2. Under the influence of pressure exerted by the operator's finger (not shown) on trigger 14, exterior cylindrical portion 61 moves rearwardly to the position shown in FIG. 4 thus sliding within mating recess 23. Since the interior wall 62 of exterior cylindrical portion 61 is in sliding contact with the exterior surface wall 63 of cylindrical inner support 60, there is negligible leakage of exterior ambient air there along, thus enabling a suction-like vacuum to be created within the enlarged interior space 64 shown in FIG. 4.

Mechanism 52 comprises a pair of butterfly valves 70 and 71 (FIG. 4) which include resilient diaphragms 72 and 73, respectively, discharge diaphragm 72 is seated against supporting member 74 and is retained in place by a suitable means such as projection 75 that is retained in place within mating cavity 76. Analogously, projections 77 and 78 which are shown as extending through base portion 79 of exterior cylindrical portion 61, retain resilient diaphragms 73 and its position a shown.

Further reference to FIG. 4 will reveal that the end 51 of conduit 50 terminates immediately at the inner surface of resilient diaphragms 73. Accordingly, and since conduit 50 is made of resilient material and can readily flex, when trigger 14 is moved toward the rear and interior space 54 begins to enlarge, the following events occur. As suction begins to develop within enlarge interior space 64, exterior atmospheric pressure against resilient diaphragm 72 maintains it in its closed position. At the same time, suction within chamber 64 begins to draw resilient diaphragm 73 away from its mating surfaces on base portion 79, thereby permitting air from within conduit 50 to move thereinto. The movement of air from within conduit 50 to space 64 of course, develops suction within conduit 50 which is communicated through the conduit to the interior of removable cup 19. Thence it is communicated through the interior of conduit 16 (FIGS. 2 and 3) to the adapter 17 or other front end of conduit 16 (FIG. 1). Thus, actuation of the trigger 14 is effective to move the trigger toward the rear, creating enlarged interior space within the suction producing mechanism, creating suction therein, extending the suction to conduit 50 into the interior 54 of removable cup 19 and thence through conduit 16 to the adapter 17 or other point of application to a body cavity.

It will now be observed that fluid sucked into conduit 16 by the suction imparted thereto as described above, traverses conduit 16 and enters through interior 56 of conduit 16 (FIGS. 2 and 3) into the interior 54 of removable cup 19 where it is retained under the influence of gravity so long as the aspirator is held in an upright position.

When the trigger is released, the action of springs 40 and 41 are effective to move the trigger forwardly to the quiescent or inactivated position as shown in FIG. 2, thus eliminating most of the volume within enlarged interior space 64. As this occurs, pressure within space 64 tends to increase, thereby forcing resilient diaphragm 73 against its base portion 79, thereby closing the same. At the same time, the pressure is effective to push resilient diaphragm 73 away from engagement with supporting member 74, thereby opening butterfly valve 70 and permitting the atmosphere within space 64 to be vented to the exterior.

It is, thus, evident that the health care provider is at all times shielded from the aspirate during suctioning and after aspiration is completed can simply remove specimen collecting cup 19 for laboratory study of the contents and dispose of the remainder of the device.

The various elements of the aspirating device are formed from materials conventionally used in medical devices. Thus, for example, aspirator main housing 11 can be formed of any approved plastic, springs 40 and 41 can be made of any suitable metal, removable cup 19 of an approved plastic, and conduit 16 of a flexible plastic suitable for insertion into humans.

While the proportions of the various elements of the device can vary widely, it is preferred to maintain the proportions such that the device can fit snugly in the hand of the average adult.

The terms and expressions used herein are employed as terms of description and not of limitation; and consequently, there is no intent in the use thereof of excluding any and all equivalents, but on the contrary, it is intended to include all adaptations and modifications that may be employed without departing from the spirit and scope of the invention as defined in the claims.

What is claimed is:

1. A hand-held aspirating device comprising a main housing having a handle and a barrel, said barrel having a front end and a rear portion, said handle having a lower end and an upper end communicating with said rear portion of said barrel; actuating means extending from said main housing beneath said barrel, means operatively associated with said actuating means to normally maintain said actuating means in an extended position, said actuating means being actuable in a direction generally parallel to said barrel to move said actuating means rearwardly toward said handle; suction means including a suction chamber disposed within said housing and responsive to the actuation of said actuating means for creating a suction within said suction chamber; a container means for receiving aspirate, said container means being removably connected to said handle; a first conduit within said housing, said first conduit having two ends, one of said ends normally being in fluid-flow communication with said container means and the other end being connected to said suction chamber; a second conduit depending from said front end of said barrel and projecting outwardly therefrom, said second conduit having two ends, one for inserting into a body cavity, the other one end being in fluid-flow communication with said container means; whereby when said actuating means is actuated and said suction is created within said suction chamber, said suction is communicated through said first conduit from said suction chamber to said container means and thence through said second conduit to said one of said two ends of said second conduit thereby to aspirate fluids from said body cavity through said second conduit into said container means.

2. The device of claim 1 wherein said actuating means is a trigger and said means associated therewith is at least one spring.

3. The device of claim 2 wherein said means is a cup.

4. The device of claim 3 wherein said suction means includes a pair of butterfly valves having resilient diaphragms, with said other one end of said first conduit normally terminating at a surface of one of said diaphragms.

5. The device of claim 4 wherein there is one butterfly valve at each end of said suction chamber.

6. A hand-held aspirating device comprising a pistol-shaped housing having a generally horizontally disposed barrel and a generally vertically disposed handle, the rear end of said barrel communicating with the upper end of said handle; a trigger extending from said handle beneath said barrel; spring loading operatively associated with said trigger to normally maintain said trigger in an extended position away from said handle, said trigger being actuable in a direction generally parallel to said barrel to move said trigger rearwardly toward said handle; suction means disposed in said housing and including a suction chamber having two ends with a butterfly valve at each end, each of said valves having a resilient diaphragm; a cup removably mounted in the bottom end of said handle, at least said bottom end and said cup being substantially transparent; a first flexible conduit located in said housing and having two ends, one of said ends normally being in fluid-flow communication with said cup and the other end being normally terminating at a surface of one of said diaphragms; a second flexible conduit having two ends and extending from a position in said housing outwardly from the front end of said barrel, one of said ends being in fluid-flow communication with said cup and the other end adapted to be inserted into a body cavity.

* * * * *